US00PP33771P2

(12) United States Plant Patent
Van Dijk

(10) Patent No.: US PP33,771 P2
(45) Date of Patent: Dec. 21, 2021

(54) ***ANTHURIUM* PLANT NAMED 'ANTHGLAM'**

(50) Latin Name: ***Anthurium andraeanum* L.**
Varietal Denomination: ANTHGLAM

(71) Applicant: ANTHURA B.V., Bleiswijk (NL)

(72) Inventor: Jan Van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 17/300,576

(22) Filed: Aug. 25, 2021

(51) Int. Cl.
*A01H 5/02* (2018.01)
*A01H 6/00* (2018.01)

(52) U.S. Cl.
USPC ..... Plt./365
CPC ..... *A01H 6/00* (2018.05)

(58) Field of Classification Search
USPC ..... Plt./365
CPC ..... A01H 5/02
See application file for complete search history.

*Primary Examiner* — Kent L Bell
(74) *Attorney, Agent, or Firm* — Jondle & Associates, P.C.

(57) ABSTRACT

A new, very small, compact, and rich in shooting *Anthurium* plant named 'ANTHGLAM' particularly distinguished by having a high number of medium glossy and weakly blistered, pink, concave and ovate, durable spathes that retain the original color for a long period of time, with green, small, deltoid leaves, red, short spadices with red tips, early and rich flowering continuously throughout the year, and a plant height of 17.0 cm to 23.0 cm is disclosed.

3 Drawing Sheets

Genus and species: *Anthurium andraeanum* L.
Variety denomination: 'ANTHGLAM'.

BACKGROUND OF THE NEW PLANT

The present invention comprises a new and distinct variety of *Anthurium*, botanically known as *Anthurium andraeanum* L., and hereinafter referred to by the variety name 'ANTHGLAM'. The new *Anthurium* plant is a product of a planned breeding program conducted by the inventor in Bleiswijk, the Netherlands. The objective of this breeding program was to create a new plant with a height of 17.0 cm to 23.0 cm having medium glossy and weakly blistered, concave, pink, ovate, and durable spathes.

The new variety originated from a cross-pollination made in March 2011 in Bleiswijk, the Netherlands. The female parent was a red *Anthurium* pot plant designated 'ANTHDINWAQ' (U.S. Plant Pat. No. 26,048), and the male parent was a red *Anthurium* pot plant designated '15750-02' (unpatented).

A single plant was selected from the progeny of the stated cross in February 2013. Asexual reproduction of the new variety by tissue culture in 2016 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Nov. 12, 2019 (Application no. 2019/2951), by Applicant who obtained the subject matter disclosed directly from the inventor. 'ANTHGLAM' has not been made publicly available or sold anywhere in the world prior to the effective filing date of this application with the exception of sales or disclosures made one year or less before the effective filing date of this claimed invention by Applicant who obtained 'ANTHGLAM' directly from the inventor.

SUMMARY OF THE INVENTION

The following are the most outstanding and distinguishing characteristics of this new variety when grown under normal horticultural practices in Bleiswijk, the Netherlands:

1) Medium glossy and weakly blistered, pink, concave, ovate spathes;
2) Red, short spadices with red tips;
3) Green, deltoid leaves;
4) Some spathes make an extra-small spathe; and
5) Plant is very small, compact, rich in shooting, and has a high number of spathes.

DESCRIPTION OF THE PHOTOGRAPHS

This new *Anthurium* plant is illustrated by the accompanying photographs which show the overall plant habit including blooms, buds, and foliage of the plant; the colors shown are as true as can be reasonably obtained by conventional photographic procedures. The photographs are of a 28-week-old plant grown in a greenhouse in Bleiswijk, the Netherlands, in June 2021. Colors in the photographs may differ from the color values cited in the detailed botanical description, which accurately describe the actual colors of the new variety.

DESCRIPTION OF THE NEW VARIETY

Figure 1:
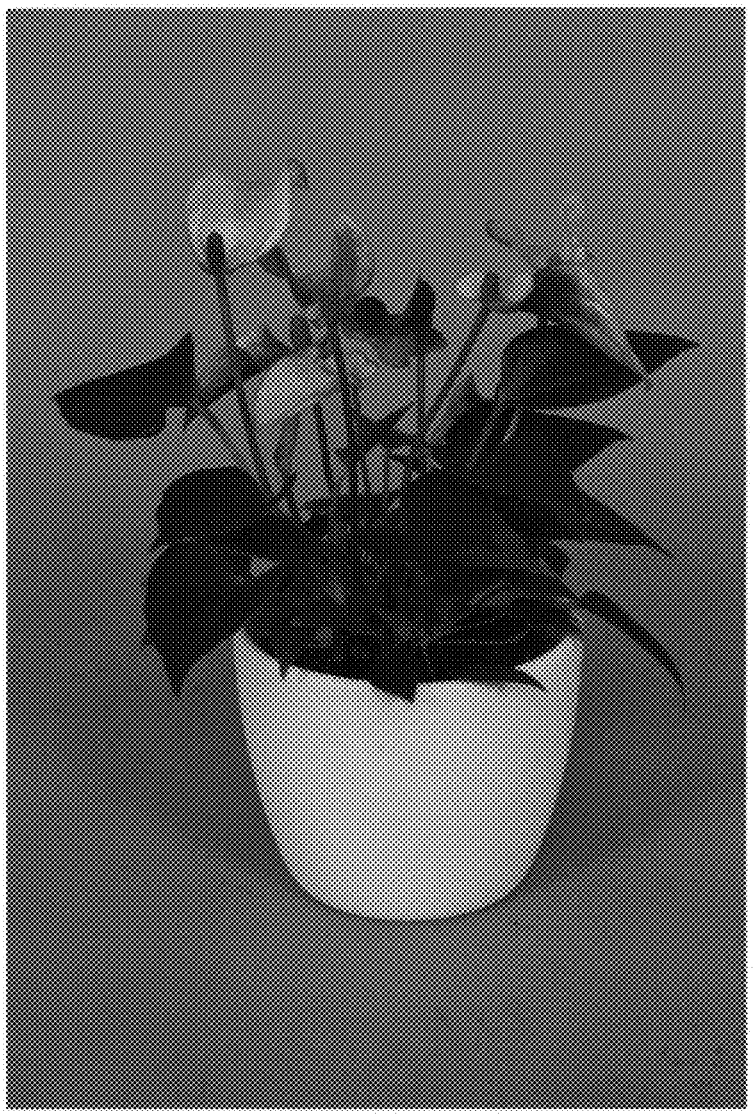
FIG. 1 shows the overall plant habit, including blooms, buds, and foliage.
Figure 2:
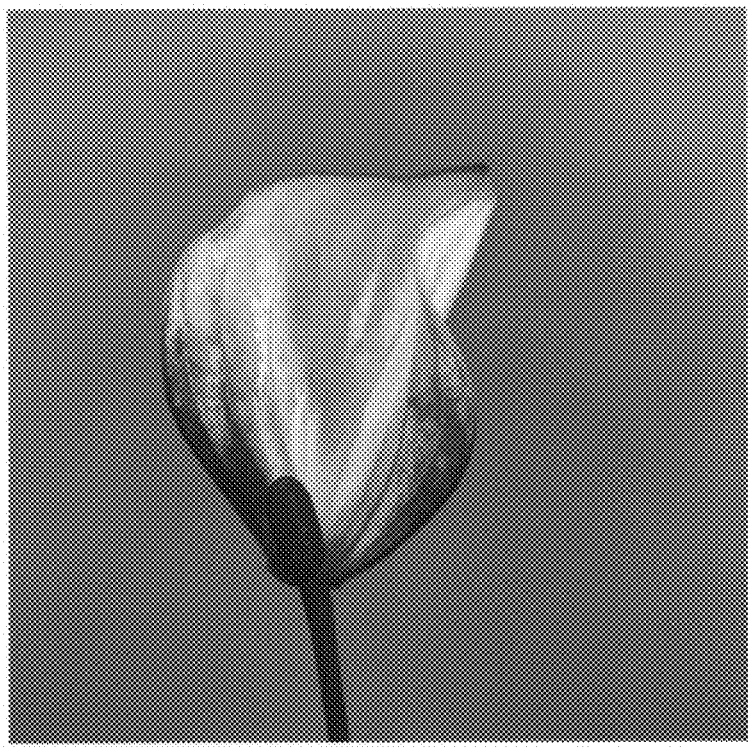
FIG. 2 shows a close-up of the mature spathe.

The following detailed description sets forth the distinctive characteristics of 'ANTHGLAM'. The data which define these characteristics were collected from asexual reproductions carried out in Bleiswijk, the Netherlands. The plant history was taken on 28-week-old plants which were planted from tissue culture in 9-centimeter (diameter) pots and grown in a glass greenhouse between 19° C. and 24° C. Observations were made in June 2021. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'ANTHGLAM'.

Parentage:

*Female parent*.—*Anthurium* plant 'ANTHDINWAQ' (U.S. Plant Pat. No. 26,048).

*Male parent*.—*Anthurium* plant '15750-02' (unpatented).

Plant:

*Propagation*.—Tissue culture.

*Root description*.—Fleshy-creamy (RHS 160C) colored roots with a touch of reddish-orange (RHS 179B and RHS 179C) with small hairy lateral roots having small yellow (RHS 9A) colored root tips.

*Time to produce a finished flowering plant*.—28 to 30 weeks after planting in a 9-cm (diameter) pot.

*Growth habit*.—Upright.

*Height* (*measured from soil, including inflorescence*).—17.0 cm to 23.0 cm.

*Width* (*measured from leaf tips*).—17.0 cm to 20.0 cm.

Leaves:

*Immature leaves*.—Length: 5.0 cm to 7.0 cm. Width: 3.0 cm to 5.0 cm. Color: Upper surface: RHS 146A. Lower surface: RHS 146B. Texture (both upper and lower surfaces): Glossy, leathery, and thin.

*Mature leaves*.—Length (fully expanded): 7.0 cm to 9.0 cm. Width: 4.0 cm to 6.0 cm. Shape: Deltoid. Apex: Acuminate. Base: Cordate. Leaf blade angle with the petiole: Between 120 degrees and 135 degrees. Leaf margin: Entire. Color: Upper surface: RHS 147A. Lower surface: RHS 146A. Texture: Upper surface: Leathery and thick. Lower surface: Glossy, leathery, and thick. Venation: Pinnate veining; the mid-vein and primary veins (the veins that radiate out from the junction of petiole and leaf) protrude at the underside of the leaf blade. Venation color: Upper surface: RHS 144A. Lower surface: RHS N144A.

*Lobes*.—Absent.

*Petiole*.—Cross-section: Round. Diameter: 0.2 cm to 0.3 cm. Length: 7.0 cm to 9.0 cm for a mature leaf size. Color: Mature leaf: RHS 144B. Immature leaf: RHS 144C. Cataphyll color surrounding the petiole: Outside: RHS 144C. Inside: RHS 144D.

*Geniculum*.—Length: 1.0 cm to 1.5 cm. Width: 0.2 cm to 0.3 cm. Color: RHS 144A.

Inflorescence:

*Arrangement*.—Single.

*Flowering habit* (*length of flowering season*).—Continuous.

*Number of inflorescences per plant*.—8 to 10.

*Fragrance*.—Absent.

*Longevity of inflorescence on plant*.—Over a half-year.

Spathe:

*Buds*.—The spathe is tightly rolled around the spadix and extrudes from the peduncle sheath. After the spathe is fully opened the peduncle elongates some extra centimeters.

*Arrangement*.—Spathe angle with the peduncle is between 90 degrees and 110 degrees; the spathe stands on a wiry peduncle about 2.0 cm to 5.0 cm above the foliage.

*Shape*.—Ovate.

*Shape in cross section of middle zone*.—Concave.

*Apex*.—Abruptly acuminate.

*Base*.—Cordate.

*Texture*.—Medium glossy and weakly blistered.

*Margin*.—Undulated.

*Size*.—Length: 5.5 cm to 6.5 cm. Width: 4.0 cm to 5.0 cm.

*Lobes*.—Absent.

Figure 3:
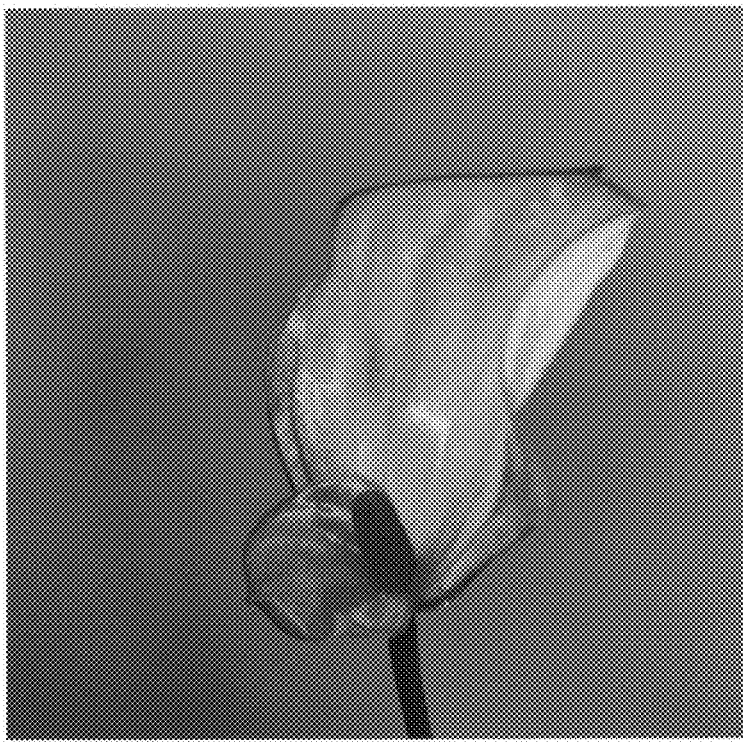
FIG. 3 shows a close-up of a spathe with an extra-small spathe.
Figure 4:
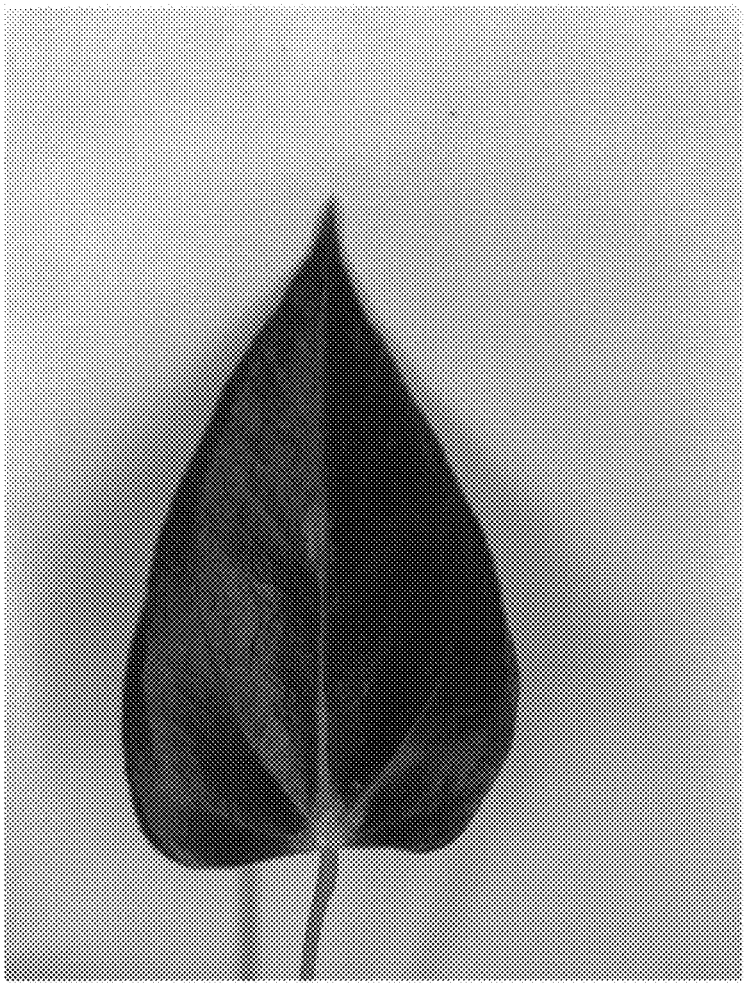
FIG. 4 shows a close-up of the upper leaf blade surface.

*Color*.—Just fully open: Upper surface: Touch of green (RHS 144A) at the base toward sides; pink (RHS 50C) with red margins (RHS 50A) toward the tip. Lower surface: Yellow-green (RHS 144C) at the base toward sides; light yellow (RHS 160D) with a pinkish-white overcolor (RHS N155C). Some spathes make an extra-small spathe having a color in between RHS 50A and RHS 50B, as shown in FIG. 3.

Peduncle:

*Shape*.—Erect.

*Cross-section*.—Round.

*Length*.—10.0 cm to 13.0 cm.

*Diameter*.—0.2 cm to 0.3 cm.

*Color*.—RHS 144B.

Flowering time:

*General*.—One small, rooted, untreated tissue culture plant of 8.0 cm tall will flower, depending on the season, after 28 to 30 weeks and 8 to 9 blossoms appear. More blossoms appear after some additional weeks so that a full flowering and commercial plant will have 9 to 10 pink spathes. Smaller blossoms may occur on immature plants.

Spadix:

*Size*.—Length: 1.0 cm to 1.5 cm (depending on flower size). Width (at apex): 0.4 cm to 0.5 cm. Width (at base): 0.5 cm to 0.6 cm.

*Shape*.—Columnar.

*Angle of spadix tip with peduncle*.—170 degrees to 180 degrees.

*Texture*.—When the spathe is unfurling, the spadix is smooth. When the spadix matures, small stigmata protrude. The stigmata are evenly distributed around the spadix. The spadix matures from base to top, slowly giving the spadix a somewhat rough appearance.

*Color*.—Immature: RHS N45A. Mature: RHS 185B. Ages to: RHS 183C.

Flowers:

*Quantity per spadix*.—30 to 50.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 158A.

Reproductive organs:

*Stamens*.—Not visible.

*Pollen amount*.—Absent.

*Pistil*.—Quantity: 30 to 50. Length: Less than 0.01 cm. Color: RHS 158A.

*Style*.—Not observed to date.

*Stigma*.—Shape: Ovoid. Diameter: Less than 0.01 cm. Color: RHS 158A.

*Ovary*.—Rarely visible.

*Ovary color*.—Not measured.

Fruit and seed set: None observed to date.

Disease and pest resistance: No specific resistance or susceptibility observed to pathogens or pests common to *Anthurium* under commercial conditions to date.

COMPARISON WITH PARENTAL AND SIMILAR COMMERCIAL VARIETIES

'ANTHGLAM' differs from the female parent plant 'ANTHDINWAQ' (U.S. Plant Pat. No. 26,048) in that 'ANTHGLAM' has deltoid leaves and spathes that are concave in cross section of middle zone, whereas 'ANTHDINWAQ' has ovate leaves and spathes that are flat in cross section of middle zone.

'ANTHGLAM' differs from the male parent plant '15750-02' (unpatented) in that 'ANTHGLAM' has spathes that are concave in cross section of middle zone, whereas '15750-02' has spathes that are flat in cross section of middle zone. Additionally, 'ANTHGLAM' has shorter spadices than '15750-02'.

'ANTHGLAM' differs from similar commercial variety 'ANTHEUYK' (U.S. Plant Pat. No. 31,417) in that 'ANTHGLAM' has ovate spathes and deltoid leaves, whereas 'ANTHEUYK' has orbicular-cordate spathes and ovate-cordate leaves. Additionally, 'ANTHGLAM' has shorter leaves and shorter spadices than 'ANTHEUYK'.

'ANTHGLAM' differs from similar variety 'ANTHOSZMO' (U.S. Plant Pat. No. 31,416) in that 'ANTHGLAM' has red spadices with red tips, whereas 'ANTHOSZMO' has pink spadices with orange-light green tips. Additionally, 'ANTHGLAM' has shorter leaves and shorter spadices than 'ANTHOSZMO'.

I claim:

1. A new and distinct variety of *Anthurium* plant named 'ANTHGLAM', substantially as illustrated and described herein.

* * * * *